United States Patent [19]

Masuda

[11] Patent Number: 4,499,085

[45] Date of Patent: Feb. 12, 1985

[54] METHOD OF ANOXIA TREATMENT USING PROSTAGLANDIN ANALOGUES

[75] Inventor: Yoshinobu Masuda, Katano, Japan

[73] Assignee: Ono Pharmaceutical Co., Ltd., Osaka, Japan

[21] Appl. No.: 490,223

[22] Filed: Apr. 29, 1983

[30] Foreign Application Priority Data

Apr. 30, 1982 [JP] Japan .................................. 57-74175
Oct. 20, 1982 [JP] Japan ................................. 57-185022

[51] Int. Cl.$^3$ ...................... A61K 31/70; A61K 31/40
[52] U.S. Cl. ..................................... 514/58; 514/415; 514/469; 514/530; 514/573; 514/690
[58] Field of Search ............... 424/274, 317, 305, 285, 424/180

[56] References Cited

PUBLICATIONS

Pickard et al., Chem. Abst., vol. 96 (1982), p. 29211n.
Pickard et al., Chem. Abst., vol. 93 (1980), p. 198269f.

Primary Examiner—Sam Rosen
Attorney, Agent, or Firm—Stevens, Davis, Miller & Mosher

[57] ABSTRACT

The invention provides a new method for the treatment of anoxia of brain cells using a $PGI_1$ derivative of the formula:

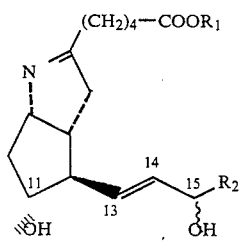

wherein $R_1$ represents hydrogen or lower alkyl and $R_2$ represents 2-methylhexyl, 3-propylcyclopentyl, 3-butylcyclopentyl or 4-propylcyclohexyl, a $PGI_2$ derivative of the formula:

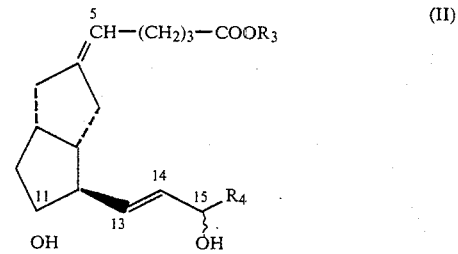

wherein $R_3$ represents hydrogen or lower alkyl and $R_4$ represents 2-methylhexyl, cyclopentyl, 3-propylcyclopentyl, or cyclohexyl, a $PGI_2$ derivative of the formula:

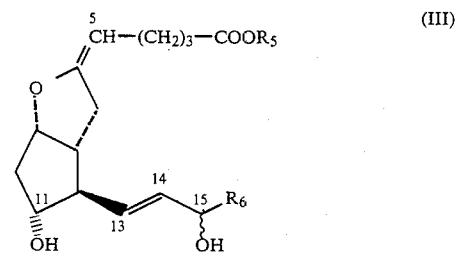

wherein $R_5$ represents lower alkyl and $R_6$ represents pentyl, 1-methylpentyl, 1-methyl-5-chloropentyl, 2-methyl-5-chloropentyl, 3-ethylcyclopentyl, 3-propylcyclopentyl, 3-butylcyclopentyl, 3-(2-chloroethyl)cyclopentyl, cyclohexyl, 4-ethylcyclohexy, or cyclohexylmethyl or a $PGE_1$ derivative of the formula:

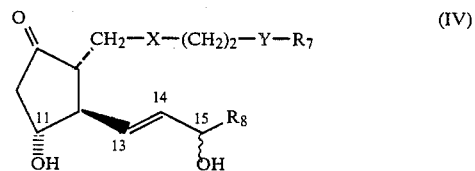

wherein X represents methylene or carbonyl and (i) when X represents methylene, Y represents ethylene or trans-vinylene, $R_7$ represents carboxy or lower alkoxycarbonyl and $R_8$ represents 2-methylhexyl or 1-cyclohexylethyl and (ii) when X represents carbonyl, Y represents ethylene, $R_7$ represents carboxyl, lower alkoxycarbonyl, glycoloyl or hydroxymethyl and $R_8$ represents 2-methylhexyl, cyclopentyl, 3-propylcyclopentyl, or 3-butylcyclopentyl or a cyclodextrin clathrate or non-toxic salt thereof.

18 Claims, No Drawings

METHOD OF ANOXIA TREATMENT USING PROSTAGLANDIN ANALOGUES

The present invention relates to a new method for the prevention or treatment of anoxia of brain cells using certain derivatives of prostaglandin I₁ (hereinafter referred to as PGI₁), prostaglandin I₂ (hereinafter referred to as PGI₂) or prostaglandin E₁ (hereinafter referred to as PGE₁), or cyclodextrin clathrates thereof, or non-toxic salts thereof.

It is already known that PGI₁, PGI₂ and PGE₁ derivatives possess, for example, activity in preventing blood platelet aggregation, activity in relaxing blood smooth muscle and activity in preventing gastric acid secretion (S. Moncada and J. R. Vane, Prostacyclin in Perspective, Prostacyclin, edited by J. R. Vane and S. Bergstrom, Raven Press, New York, 1979). The present invention, however, utilises a new and surprising activity of such derivatives, in the treatment of anoxia in brain cells.

Unlike other organs of the body, the brain is present in a specific environment in a rigid body, such as the skull or the cerebral pachymeninx, immersed in cerebrospinal fluid, and is one of the most active organs in energy metabolism, having the maximum rate of oxygen consumption among the various organs of the living body. Most of the energy required for nerve cells of the brain is derived from oxygen and glucose but sources of these are hardly stored in the brain and are always supplied from the blood stream. Therefore, a mechanism for controlling the flow of the cerebral blood is well developed to stably supply the energy sources of the cerebral tissue and maintain the external environment of the brain cells constant. When the homeostatic mechanism of the brain fails due to physical compression arising from, for example, hematoma, tumor or trauma, brain cells are exposed to a state in which oxygen is deficient and the brain cannot function normally. The state in which oxygen is deficient (hereinafter referred to as brain anoxia) results in a change of the membrane permeability of brain cells so that edema is caused by endosmosis of extracellular fluids. As cerebral edema grows to a certain extent, brain pressure increases and circulation disturbance in the brain is caused. Accentuation of brain anoxia and glucose deficiency, as well as accumulation of its metabolites, due to the circulation disturbance promote cerebral edema so that cerebral edema and brain pressure further increase and compression of the brain stem and disturbance in the passage of cerebrospinal fluid occur; increased brain anoxia, acceleration of cerebral edema and accentuation of brain pressure result from this vicious circle. The focus of the disturbance is thus enlarged so that previously normal brain tissue suffers brain anoxia in which the brain suffers circulatory insufficiency and the disturbance becomes serious. This is the reason why oxygen tissular insufficiency is the common denominator of most cerebral diseases [Eur. Neurol. 17 (Supple. 1), 113 (1978)].

At present, hypnonarcotic agents, such as phenobarbital and thiobarbital, are employed to treat anoxic diseases of brain cells. Hypnonarcotic agents inhibit nerve action of the brain so that the energy requirement of brain cells decreases and a protective action on nerve cell function occurs. In other words, hypnonarcotic agents exert their action by forcibly reducing the nerve cell function to a level lower than normal. The dose of such agents sufficient to produce the desired effect therefore affects the entire central nervous system. As a result, they exert an adverse influence on respiratory organs and circulatory organs, in the prevention of respiration or in their effect on the blood pressure-controlling center.

Accordingly, it has been strongly desired to develop medicines free from the side effects caused by hypnonarcotic agents but exhibiting excellent therapeutic effects at a low dose, in the prevention or treatment of anoxia of brain cells.

As a result of extensive investigations, it has now been found that certain PGI₁ derivatives, PGI₂ derivatives and PGE₁ derivatives exhibit an excellent protective action against brain anoxia at a low dose, and their action is not based on the reduction of brain cell function.

The present invention accordingly provides a method for the treatment (which may be preventive treatment) of anoxia of brain cells in a mammalian host, which comprises administering to a host suffering from, or subject to, such anoxia at least one PGI₁ derivative of the general formula:

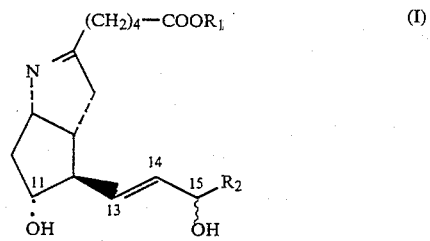

wherein R₁ represents a hydrogen atom or a lower alkyl group and R₂ represents a 2-methylhexyl group, a 3-propylcyclopentyl group, a 3-butylcyclopentyl group or a 4-propylcyclohexyl group, PGI₂ derivative of the general formula:

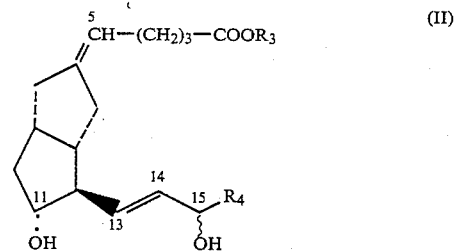

wherein R₃ represents a hydrogen atom or a lower alkyl group and R₄ represents a 2-methylhexyl group, a cyclopentyl group, a 3-propylcyclopentyl group or a cyclohexyl group, PGI₂ derivative of the general formula:

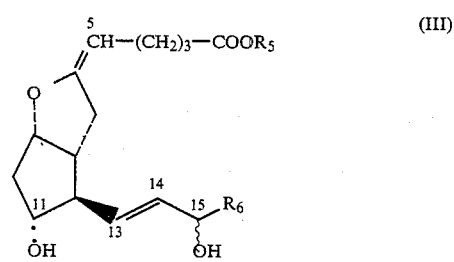

wherein $R_5$ represents a lower alkyl group and $R_6$ represents a pentyl group, a 1-methylpentyl group, a 1-methyl-5-chloropentyl group, a 2-methyl-5-chloropentyl group, a 3-ethylcyclopentyl group, a 3-propylcyclopentyl group, a 3-butylcyclopentyl group, a 3-(2-chloroethyl)cyclopentyl group, a cyclohexyl group, a 4-ethylcyclohexyl group or a cyclohexylmethyl group, or $PGE_1$ derivative of the general formula:

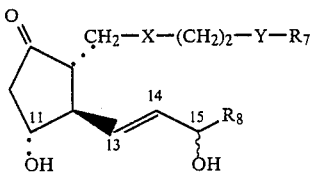

wherein X represents a methylene group or a carbonyl group, and (i) when X represents a methylene group, Y represents an ethylene group or a trans-vinylene group, $R_7$ represents a carboxy group or a lower alkoxycarbonyl group and $R_8$ represents a 2-methylhexyl group or a 1-cyclohexylethyl group, and (ii) when X represents a carbonyl group, Y represents an ethylene group, $R_7$ represents a carboxyl group, a lower alkoxycarbonyl group, a glycoloyl group or a hydroxymethyl group and $R_8$ represents a 2-methylhexyl group, a cyclopentyl group, a 3-propylcyclopentyl group or a 3-butylcyclopentyl group, the double bonds between $C_{13}$–$C_{14}$ in general formulae (I), (II), (III) and (IV) being trans, the configuration at $C_5$ in general formulae (II) and (III) being E or Z or a mixture thereof, the hydroxy groups attached to the $C_{11}$ position in general formulae (I), (II), (III) and (IV) being in α-configuration, and the hydroxy groups attached to the $C_{15}$ position in general formulae (I), (II), (III) and (IV) being in α- or β-configuration, or a mixture thereof, preferably in α-configuration, or cyclodextrin clathrate of a derivative of general formula (I), (II), (III) or (IV) above, or, when $R_1$ in general formula (I) or $R_3$ in general formula (II) represents a hydrogen atom, or $R_7$ in general formula (IV) represents a carboxyl group, non-toxic salt thereof.

In this specification and the accompanying claims lower alkyl groups are straight- or branched-chain and have 1 to 4 carbon atoms (and are preferably methyl), and lower alkoxy groups are straight- or branched-chain and have 1 to 4 carbon atoms (and are preferably methoxy).

$PGI_1$ derivatives of general formula (I), $PGI_2$ derivatives of general formulae (II) and (III), and $PGE_1$ derivatives of general formula (IV) as well as cyclodextrin clathrates thereof and salts thereof can be prepared by the application or adaptation of methods heretofore used or described in the chemical literature. Suitable processes are described in the specifications of the U.S. Pat. Nos. 3,931,296, 3,966,792, 4,178,367, 4,205,178, 4,215,142, 4,232,009, 4,234,597, 4,294,849 and 4,313,954, in the specifications of the German Patent Publication Nos. 2365035, 2409460, 2525897, 2753986, 2807178, 2840032, 2906699, 2909361, 2912409, 3002677 and 3006032, in the specifications of the Belgian Pat. Nos. 782822, 809169, 811665, 862547, 870531 and 881799 in the Specification of the European Patent Publication No. 68871, and in J. Amer. Chem. Soc., 99(12), 4182 (1977).

Preferred prostaglandin derivatives for use in the method of the present invention are 16,19-ethano-ω-dihomo-6,9α-nitrilo-$PGI_1$ methyl ester, 17(S)-methyl-ω-homo-6,9α-nitrilo-$PGI_1$, 15-cyclopentyl-ω-pentanor-5E-6,9α-methano-$PGI_2$, 15-cyclohexyl-ω-pentanor-$PGI_2$ methyl ester, 16,19-ethano-ω-homo-$PGI_2$ methyl ester, 17(S)-methyl-ω-homo-trans-$\Delta^2$-$PGE_1$, 15-cyclopentyl-ω-pentanor-6-keto-$PGE_1$ methyl ester, 2-decarboxy-2-glycoloyl-15-cyclopentyl-ω-pentanor-6-keto-$PGE_1$, 17(S)-methyl-ω-homo-6-keto-$PGE_1$ alcohol, 16,18-ethano-ω-dihomo-6-keto-$PGE_1$ alcohol and cyclodextrin clathrates thereof; especially preferred derivatives are 16,19-ethano-ω-dihomo-6,9α-nitrilo $PGI_1$ methyl ester, 17(S)-methyl-ω-homo-6,9α-nitrilo-$PGI_1$, 15-cyclohexyl-ω-pentanor-$PGI_2$ methyl ester, 16,19-ethano-ω-homo-$PGI_2$ methyl ester and 17(S)-methyl-ω-homo-trans-$\Delta^2$-$PGE_1$ and cyclodextrin clathrates thereof.

The method of the present invention may be employed in the treatment of brain anoxia caused by, for example, intracranial disease, since the agents possess a protective action against brain anoxia.

Moreover, the derivatives used in the method of the present invention do not exhibit side effects such as suppression of breathing or circulatory insufficiency arising from inhibition over the entire central nervous system since the protective action on brain cell function is not caused by the inhibition of nerve action of the brain as caused by hypnonarcotic agents conventionally used for treatment of anoxia of brain cells. Furthermore, hypnonarcotic agents could be administered only at an acute stadium, whereas it is possible to carry out the method of the present invention at a chronic stadium and for the purpose of preventing relapse of attack as the prostaglandin derivatives used exert no hypnonarcotic action.

The prostaglandin derivatives used in accordance with the present invention exhibit a protective action against anoxia of the brain at a low dose and have a potent action. In addition, their toxicity is low and accordingly their safety in use is high. For example, 16,19-ethano-ω-dihomo-6,9α-nitrilo-$PGI_1$ methyl ester does not cause lethality when subcutaneously administered to mice at a 30 mg/kg dose, a dose which is more than 300 times the minimum effective dose.

In the method of the present invention, $PGI_1$ derivatives represented by the general formula (I) or $PGI_2$ derivatives represented by the general formula (II) are characterized by a prolonged duration of activity, or an enhanced strength of activity in oral administration, and the most preferred compounds of them include 16,19-ethano-ω-dihomo-6,9α-nitrilo-$PGI_1$ methyl ester and 17(S)-methyl-ω-homo-6,9α-nitrilo-$PGI_1$. $PGI_2$ derivatives represented by the general formula (III) are characterized by a rapid appearance of activity or an especially enhanced strength of activity in parenteral administration, and the most preferred compounds of them include 15-cyclohexyl-ω-pentanor-$PGI_2$ methyl ester and 16,19-ethano-ω-homo-$PGI_2$ methyl ester. $PGE_1$ derivatives represented by the general formula (IV) are characterized by a prolonged duration of activity or an enhanced strength of activity in both oral and parenteral administration, and the most preferred compound of them is 17(S)-methyl-ω-homo-trans-$\Delta^2$-$PGE_1$.

$PGI_1$ derivatives represented by the general formula (I), $PGI_2$ derivatives represented by the general formulae (II) and (III), and $PGE_1$ derivatives represented by the general formula (IV) may be used in the form of pharmaceutical compositions which comprise a derivative represented by the general formula (I), (II), (III) or (IV), or cyclodextrin clathrate thereof, or non-toxic salt thereof, together with a pharmaceutical carrier or coating.

In clinical practice, for the prevention or treatment of anoxia of brain cells, the compounds represented by the general formula (I), (II), (III) or (IV), or cyclodextrin clathrate thereof, or non-toxic salt thereof will normally be administered systemically or partially, usually by oral or parenteral (e.g. intravenous, subcutaneous or intramuscular) administration.

Solid compositions for oral administration include compressed tablets, pills, dispersible powders and granules. In such solid compositions, one or more of the active compound(s) is, or are, admixed with at least one inert diluent such as lactose, mannitol, glucose, hydroxypropyl cellulose, microcrystalline cellulose, starch, polyvinylpyrrolidone or magnesium metasilicate aluminate. The compositions may also comprise, as is normal practice, additional substances other than inert diluents e.g. lubricating agents such as magnesium stearate, and disintegrating agents, such as cellulose calcium glucolate. The tablets or pills may, if desired, be made into enteric film-coated or gastric film-coated tablets or pills, such as sugar-coated, gelatin-coated, hydroxypropylcellulose-coated or hydroxypropylmethylcellulose phthalate-coated tablets or pills; two or more layers may be used.

The compositions for oral administration also include capsules of absorbable material such as gelatin, containing one or more of the active substances with or without the addition of diluents or excipients.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions for oral administration include spray compositions which may be prepared by known methods and which comprise at least one compound of the present invention.

Preparations for parenteral administration include sterile aqueous or non-aqueous solutions, suspensions or emulsions. Examples of aqueous solvents or suspending media are distilled water for injection and physiological salt solution. Examples of non-aqueous solvents or suspending media are propylene glycol, polyethylene glycol, vegetable oils such as olive oil, alcohols such as ethanol, and Polysorbate 80 (registered Trade Mark).

These compositions may lso include adjuvants such as preserving, wetting, emulsifying and dispersing agents. They may be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

Other compositions include, for parenteral administration, liquids for external use, and endermic liniments such as ointments; suppositories for rectal administration; and pessaries for vaginal administration. Such compositions are prepared by known methods.

The percentage of active ingredient in the compositions used in the method of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance.

The dose to be administered is determined depending upon, for example, age, symptoms, the desired therapeutic effects, the route of administration, and the duration of the treatment.

The daily dosage in mammals, for example, domestic mammals such as cows, mares, sows, ewes and bitches or, preferably, in the human adult, is generally between 0.0003 and 100 mg/kg body weight, preferably between 0.0003 and 10 mg/kg body weight by intravenous, intramuscular or subcutaneous administration and preferably between 0.0003 and 30 mg/kg body weight by oral administration for the treatment of anoxia of brain cells; the active compounds can be administered up to several times, for example 3 or 4 times, per day.

As mentioned above, the doses to be used depend on various factors. Therefore, there may be cases in which doses greater than the ranges specified above, or lower than the ranges specified above, may be used.

The present invention is illustrated in more detail in the following Experimental Examples and Preparative Examples.

Compounds used are as follows: the patent or literature references in parenthesis describe a suitable process of preparation. In the following "USP" denotes "United States Patent No." and "GBP" denotes "British Patent Publication No." Physicochemical characteristics are given at the end of the Table for compounds 5, 12, 16, 19, 22, 24, 25 and 27.

| Compound No. | |
|---|---|
| 1. | 16,19-ethano-ω-dihomo-6,9α-nitrilo-PGI$_1$ methyl ester [USP-4234597, Example 2(4)] |
| 2. | 16,18-ethano-ω-homo-6,9α-nitrilo-PGI$_1$ [USP-4234597, Example 3] |
| 3. | 17(S)—methyl-ω-homo-6,9α-nitrilo-PGI$_1$ methyl ester [USP-4313954, Example 2] |
| 4. | 17(S)—methyl-ω-homo-6,9α-nitrilo-PGI$_1$ [USP-4313954, Example 3] |
| 5. | 15-cyclopentyl-ω-pentanor-5E-6,9α-methano-PGI$_2$[1] |
| 6. | 17(S)—methyl-ω-homo-6,9αmethano-5EZ—PGI$_2$ methyl ester [GBP-2017699A, Example 3(b)] |
| 7. | 15-cyclohexyl-ωpentanor-PGI$_2$ methyl ester [USP-4178367, Example 2(a)] |
| 8. | 16,19-ethano-ω-homo-PGI$_2$ methyl ester [USP-4178367, Example 2(b)] |
| 9. | PGI$_2$ methyl ester [J. Amer. Chem. Soc., 99(12), 4182 (1977)] |
| 10. | 16,18-ethano-ω-homo-PGI$_2$ methyl ester [USP-4178367, Example 2(e)] |
| 11. | 17(R)-methyl-20-chloro-PGI$_2$ methyl ester [USP-4232009, Example 2(b)] |
| 12. | 16,18-ethano-ω-dihomo-PGI$_2$ methyl ester[2] |
| 13. | 16,18-ethano-20-chloro-PGI$_2$ methyl ester [USP-4232009, Example 2(c)] |
| 14. | 16-cyclohexyl-ω-tetranor-PGI$_2$ methyl ester [USP-4178367, Example 2(c)] |
| 15. | 16(ξ)-methyl-20-chloro-PGI$_2$ methyl ester [USP-4232009, Example 2] |
| 16. | 16,18-ethano-PGI$_2$ methyl ester[3] |
| 17. | 16-cyclohexyl-ω-trinor-PGE$_1$ methyl ester [USP-3966792, Example 23] |
| 18. | 17(S)—methyl-ω-homo-trans-Δ$^2$-PGE$_1$ [USP-4294849, Example 1] |
| 19. | 17(S)—methyl-ω-homo-transΔ$^2$-PGE$_1$.αcyclodextrin |

-continued

| Compound No. | |
|---|---|
| 20. | 16,18-ethano-ω-dihomo-6-keto-PGE$_1$ methyl ester clathrate[4] [USP-4215142, Example 2(d)] |
| 21. | 2-decarboxyl-2-glycoloyl-17(S)—methyl-ω-homo-6-keto-PGE$_1$ [European Patent 68871A, Example 1(c)] |
| 22. | 15-cyclopentyl-ω-pentanor-6-keto-PGE$_1$ methyl ester[5] |
| 23. | 2-decarboxy-2-glycoloyl-15-cyclopentyl-ω-pentanor-6-keto-PGE$_1$ [European Patent 68871A, Example 1(b)] |
| 24. | 17(S)—methyl-ω-homo-6-keto-PGE$_1$ alcohol[6] |
| 25. | 16,18-ethano-ω-dihomo-6-keto-PGE$_1$ alcohol[7] |
| 26. | 2-decarboxy-2-glycoloyl-16,18-ethano-ω-homo-6-keto-PGE$_1$ [European Patent 68871A, Example 1] |
| 27. | 16,18-ethano-ω-homo-6-keto-PGE$_1$ alcohol[8] |

In the following, ratios are by volume.

(1) Thin Layer Chromatography (abbreviated as TLC hereinafter) [developing solvent; ethyl acetate:cyclohexane=3:1 (containing 2% acetic acid)]: Rf=0.23 (on silica gel).

(2) TLC[developing solvent; diethyl ether: acetone=3:1 (containing 0.1% triethylamine), using silica gel plate treated with a solution of diethyl ether and triethylamine (95:5)]: Rf=0.45.

(3) TLC[developing solvent; diethyl ether:acetone=3:1 (containing 0.1% triethylamine), using silica gel plate treated with a solution of diethyl ether and triethylamine (95:5)]: Rf=0.42.

(4) TLC(developing solvent; chloroform:tetrahydrofuran:acetic acid=10:2:1): Rf=0.26 (on silica gel).

(5) TLC(developing solvent; ethyl acetate:acetic acid=20:1): Rf=0.3(on silica gel).

(6) TLC(developing solvent; ethyl acetate): Rf=0.13.(on silica gel)

(7) Melting Point: 92°–95° C.

(8) Melting Point: 63°–65° C.

EXPERIMENTAL EXAMPLE 1

Protective Effect on Brain Anoxia by Subcutaneous Administration (i) Life-Prolongation Effect: Death Induced by Normabaric Hypoxia in Mice An amount of a compound (Compound No. 1, 3–13, 15, 17, 20–27) was dissolved in 0.1 ml of ethanol and then the solution was diluted with a 0.1M glycine-sodium hydroxide buffer solution (pH 10.0) (for Compound No. 1, 3–13, 15), or diluted with distilled water (for Compound No. 17, 20–27). For Compound No. 19, an amount of the compound was dissolved in distilled water. Each solution was subcutaneously administered to one group comprising five STD-ddY male mice weighing 20–24 g, in a proportion of 0.1 ml per 10 g of the body weight of a mouse. At the maximum activity-exhibiting time (2.0 hours with Compound No. 1, 3–6; 0.25 hour with Compound No. 7–13, 15; and 0.5 hour with Compound No. 17, 19–27), respectively, mice were put in a plastic container of 2.5 liter volume, and a low oxygen content gasous mixture composed of 4% of oxygen and 96% of nitrogen was supplied at a rate of 4 liter per minute: the time until death of the mice was measured using as an index respiratory standstill. For comparison, a 0.1M glycine-sodium hydroxide buffer solution containing the same concentration of ethanol (as to Compound No. 1, 3–13, 15), or distilled water containing the same concentration of ethanol (as to Compound No. 17, 20–27), or distilled water (as to Compound 19), was likewise administered to the control group. Results are as shown in Table 1.

TABLE 1

Life-Prolongation Effect: Death Induced by Normabaric Hypoxia in Mice (s.c.)

| Compound No. | Dose (mg/kg) | Average Survival Time (second ± standard error) |
|---|---|---|
| 1 | control | 145.0 ± 4.5 |
|  | 0.03 | 158.0 ± 6.2 |
|  | 0.30 | 185.0 ± 10.4 |
|  | 1.00 | 208.0 ± 6.4 |
| 3 | control | 188.0 ± 11.4 |
|  | 0.30 | 250.0 ± 21.9 |
| 4 | control | 238.0 ± 20.9 |
|  | 0.30 | 360.0 ± 12.7 |
|  | 3.00 | 566.0 ± 100.0 |
| 5 | control | 177.8 ± 9.0 |
|  | 3.00 | 194.0 ± 1.3 |
| 6 | control | 184.0 ± 8.1 |
|  | 1.00 | 235.0 ± 10.6 |
|  | 3.00 | 284.0 ± 19.8 |
| 7 | control | 214.2 ± 5.4 |
|  | 0.01 | 266.0 ± 10.2 |
|  | 0.10 | 291.0 ± 33.0 |
|  | 0.30 | 296.0 ± 28.4 |
| 8 | control | 180.8 ± 3.5 |
|  | 0.03 | 236.0 ± 13.9 |
|  | 0.10 | 272.0 ± 32.9 |
| 9 | control | 224.0 ± 13.7 |
|  | 0.10 | 367.0 ± 49.7 |
| 10 | control | 194.0 ± 6.1 |
|  | 0.10 | 230.0 ± 5.2 |
| 11 | control | 207.0 ± 14.5 |
|  | 0.03 | 264.0 ± 17.5 |
|  | 0.10 | 289.0 ± 24.4 |
|  | 1.00 | 327.0 ± 49.5 |
| 12 | control | 176.0 ± 8.1 |
|  | 0.10 | 244.0 ± 10.8 |
| 13 | control | 187.0 ± 8.2 |
|  | 0.03 | 264.0 ± 18.4 |
| 15 | control | 201.0 ± 12.0 |
|  | 0.10 | 278.0 ± 19.3 |
| 17 | control | 215.5 ± 12.4 |
|  | 0.03 | 238.0 ± 11.1 |
|  | 0.10 | 375.0 ± 41.4 |
|  | 0.30 | 370.0 ± 54.4 |
| 19 | control | 182.1 ± 5.0 |
|  | 0.003 | 232.0 ± 16.6 |
|  | 0.01 | 262.0 ± 25.8 |
|  | 0.03 | 377.5 ± 38.3 |
| 20 | control | 206.0 ± 16.3 |
|  | 0.01 | 266.0 ± 17.4 |
|  | 0.03 | 362.0 ± 22.5 |
| 21 | control | 192.0 ± 25.4 |
|  | 0.03 | 333.0 ± 39.8 |
|  | 0.10 | 362.0 ± 39.5 |
| 22 | control | 210.0 ± 15.6 |
|  | 0.10 | 405.0 ± 40.2 |
| 23 | control | 211.1 ± 8.4 |
|  | 0.03 | 254.0 ± 21.7 |
|  | 0.10 | 361.0 ± 36.1 |
| 24 | control | 211.1 ± 8.4 |
|  | 0.03 | 255.0 ± 11.9 |
|  | 0.10 | 418.0 ± 42.9 |
| 25 | control | 224.0 ± 13.7 |
|  | 0.03 | 287.0 ± 28.1 |
|  | 0.10 | 281.0 ± 20.9 |
|  | 0.30 | 323.0 ± 24.0 |
| 26 | control | 211.0 ± 8.4 |
|  | 0.01 | 367.0 ± 55.9 |
|  | 0.03 | 343.0 ± 22.5 |
|  | 0.10 | 393.0 ± 41.2 |
| 27 | control | 217.0 ± 14.2 |
|  | 0.10 | 289.0 ± 12.3 |
|  | 0.30 | 413.0 ± 42.6 |

A dose-effect relationship calculated by using the results in Table 1 is shown in the following Table 2.

TABLE 2

| Compound No. | PD$_{30}$ (mg/kg) |
|---|---|
| 7 | 0.05 |
| 8 | 0.03 |

PD$_{30}$: dose required to produced a 30% prolongation of average survival time (ii) Prolongation Effect on Time of Gasping Movements Induced by Complete Ischemia in Mice An amount of a compound (Compound No. 1-11, 14-18, 20-22, 24-27) was dissolved in 0.1 ml of ethanol and then the solution was diluted with a 0.1M glycine-sodium hydroxide buffer solution (pH 10.0) (for Compound No. 1-11, 14-16), or diluted with distilled water (for Compound No.17,18, 20-22, 24-27). For Compound No. 19, an amount of the compound was dissolved in distilled water. Each solution was subcutaneously administered to one group comprising five STD-ddY male mice weighing 20-24 g, in a proportion of 0.1 ml per 10 g of the body weight of a mouse. At the maximum activity-exhibiting time (2.0 hours with Compound No. 1-6; 0.25 hour with Compound No. 7-11, 14-16; and 0.5 hour with Compound No. 17-22, 24-27), respectively, the neck of the mouse was cut with scissors for decapitation and, the persistent time until gasping movements, which appeared at the separated head, disappeared was measured. For comparison, a 0.1M glycine-sodium hydroxide buffer solution containing the same concentration of ethanol (as to Compound No. 1-11, 14-16) or distilled water containing the same concentration of ethanol (as to Compound No. 17,18,20-22,24-27), or distilled water (as to Compound 19), was likewise administered to the control group. Results are as shown in Table 3.

TABLE 3

Prolongation Effect on Time of Gasping Movements Induced by Complete Ischemia in Mice (S.C.)

| Compound No. | Dose (mg/kg) | Average Persistent Time (second ± standard error) |
|---|---|---|
| 1 | control | 18.8 ± 0.4 |
|   | 0.10 | 20.6 ± 0.3 |
|   | 0.30 | 21.6 ± 0.5 |
|   | 1.00 | 23.2 ± 0.4 |
| 2 | control | 19.2 ± 0.6 |
|   | 0.10 | 21.2 ± 0.5 |
|   | 0.30 | 22.2 ± 0.5 |
|   | 1.00 | 25.6 ± 0.6 |
| 3 | control | 19.2 ± 0.4 |
|   | 0.30 | 21.6 ± 1.3 |
| 4 | control | 19.0 ± 0.3 |
|   | 0.03 | 21.4 ± 0.5 |
|   | 0.10 | 22.8 ± 1.0 |
|   | 0.30 | 23.2 ± 0.4 |
|   | 1.00 | 24.6 ± 0.7 |
|   | 3.00 | 25.8 ± 0.6 |
| 5 | control | 20.2 ± 0.6 |
|   | 1.00 | 22.3 ± 0.5 |
| 6 | control | 18.2 ± 0.4 |
|   | 0.10 | 20.8 ± 0.6 |
|   | 1.00 | 21.0 ± 0.5 |
|   | 3.00 | 22.4 ± 0.8 |
| 7 | control | 18.5 ± 0.2 |
|   | 0.01 | 19.8 ± 0.6 |
|   | 0.10 | 23.0 ± 0.7 |
| 8 | control | 18.0 ± 0.4 |
|   | 0.10 | 21.6 ± 0.8 |
|   | 1.00 | 22.8 ± 0.7 |
| 9 | control | 19.2 ± 0.5 |
|   | 0.01 | 21.2 ± 0.4 |
|   | 0.10 | 23.6 ± 0.6 |
| 10 | control | 19.0 ± 0.3 |
|   | 0.10 | 23.0 ± 0.9 |
| 11 | control | 19.8 ± 0.4 |
|   | 0.30 | 24.0 ± 1.1 |
|   | 1.00 | 25.6 ± 6.9 |
| 14 | control | 18.2 ± 0.2 |
|   | 0.03 | 19.8 ± 0.6 |
|   | 0.10 | 20.4 ± 0.4 |
|   | 0.30 | 22.2 ± 0.7 |
| 15 | control | 19.0 ± 0.8 |
|   | 0.10 | 23.6 ± 1.2 |
| 16 | control | 19.2 ± 0.7 |
|   | 0.10 | 22.0 ± 0.6 |
| 17 | control | 19.2 ± 0.6 |
|   | 0.10 | 21.8 ± 0.3 |
|   | 0.30 | 25.4 ± 0.2 |
| 18 | control | 20.2 ± 0.6 |
|   | 0.03 | 23.4 ± 1.0 |
|   | 0.10 | 25.2 ± 0.4 |
|   | 0.30 | 28.0 ± 1.0 |
| 19 | control | 20.7 ± 0.9 |
|   | 0.03 | 25.0 ± 0.6 |
|   | 0.10 | 25.1 ± 0.9 |
|   | 0.30 | 27.5 ± 1.1 |
| 20 | control | 19.2 ± 0.6 |
|   | 0.03 | 21.2 ± 1.2 |
|   | 0.10 | 26.4 ± 1.8 |
| 21 | control | 19.0 ± 0.5 |
|   | 0.10 | 22.6 ± 0.9 |
|   | 0.30 | 23.0 ± 0.5 |
|   | 1.00 | 26.2 ± 1.2 |
| 22 | control | 19.0 ± 0.5 |
|   | 0.10 | 23.0 ± 1.5 |
|   | 0.30 | 24.8 ± 0.9 |
| 24 | control | 18.6 ± 0.3 |
|   | 0.03 | 20.6 ± 0.8 |
|   | 0.10 | 21.2 ± 0.7 |
|   | 0.30 | 23.4 ± 1.0 |
| 25 | control | 18.4 ± 0.2 |
|   | 0.10 | 21.2 ± 0.8 |
|   | 0.30 | 21.8 ± 0.5 |
|   | 1.00 | 23.0 ± 1.0 |
| 26 | control | 18.6 ± 0.3 |
|   | 0.03 | 21.2 ± 0.7 |
|   | 0.10 | 23.0 ± 1.5 |
|   | 0.30 | 23.4 ± 1.0 |
| 27 | control | 18.6 ± 0.5 |
|   | 0.10 | 21.3 ± 0.6 |
|   | 0.30 | 22.8 ± 1.0 |

A dose-effect relation calculated by using the results in Table 3 is shown in the following Table 4.

TABLE 4

| Compound No. | PD$_{15}$ (mg/kg) |
|---|---|
| 4 | 0.05 |
| 7 | 0.08 |
| 8 | 0.06 |

PD$_{15}$: dose required to produce a 15% prolongation of average time of gasping movements

EXPERIMENTAL EXAMPLE 2

Protective Effect on Brain Anoxia by Oral Administration (i) Life-Prolongation Effect: Death Induced by Normabaric Hypoxia in Mice An amount of a compound (Compound No. 1, 4) was dissolved in 0.1 ml of ethanol and then the solution was diluted with a 0.1M glycine-sodium hydroxide buffer solution (pH 10.0). For Compound No. 19, an amount of the compound was dissolved in distilled water. Each solution was orally administered to one group comprising 5-10 STD-ddY male mice weighing 20-24 g, in a proportion of 0.1 ml per 10 g of the body weight of a mouse. After 0.5 hour (Compound No. 1, 4) or 2 hours (Compound No. 19) from administration, mice were put in a plastics container of 2.5 liter volume, and a low oxygen content gaseous mixture composed of 4% of oxygen and 96% of nitrogen was supplied at a rate of 4 liter per minute: the time until death of the mice as measured using as an index respiratory standstill. For comparison, a 0.1M glycine-sodium hydroxide buffer solution containing the same concentration of ethanol as the test solution, or distilled water, was likewise administered to the control group. Results are as shown in Table 5.

TABLE 5

Life-Prolongation Effect: Death Induced by Normabaric Hypoxia in Mice (p.o.)

| Compound No. | Dose (mg/kg) | Average Survival Time (second ± standard error) | Rate of Change |
|---|---|---|---|
| 1 | control | 165.0 ± 11.2 | 100.0 ± 6.8 |
|   | 0.3 | 262.0 ± 10.7 | 158.8 ± 6.5 |
|   | 1.0 | 265.0 ± 15.0 | 160.6 ± 9.1 |
|   | 3.0 | 285.0 ± 20.6 | 172.7 ± 12.5 |
| 4 | control | 165.0 ± 18.5 | 100.0 ± 11.2 |
|   | 0.1 | 206.0 ± 13.0 | 124.8 ± 7.9 |
|   | 0.3 | 231.0 ± 22.2 | 140.0 ± 13.5 |
|   | 1.0 | 247.0 ± 19.7 | 149.7 ± 11.9 |
| 19 | control | 181.5 ± 6.8 | 100.0 ± 3.7 |
|   | 0.1 | 216.5 ± 9.4 | 119.3 ± 5.2 |
|   | 0.3 | 293.5 ± 17.5 | 161.7 ± 9.6 |
|   | 1.0 | 415.3 ± 25.4 | 228.8 ± 14.0 |

(ii) Prolongation Effect on Time of Gasping Movements Induced by Complete Ischemia in Mice An amount of a compound (Compound No. 1, 4) was dissolved in 0.1 ml of ethanol and then the solution was diluted with a 0.1M glycine-sodium hydroxide buffer solution (pH 10.0). For Compound No. 19, an amount of the compound was dissolved in distilled water. Each solution was orally administered to one group comprising 5-10STD-ddY male mice weighing 20-24 g, in a proportion of 0.1 ml per 10 g of the body weight of a mouse. After 0.5 hour (Compound No. 1,4) or 2 hours (Compound No. 19) from administration, the neck of the mouse was cut with scissors for decapitation and, the persisent time until gasping movements, which appeared at the separated head, disappeared was measured. For comparison, a 0.1M glycine-sodium hydroxide buffer solution containing the same concentration of ethanol as the test solution, or distilled water was likewise administered to the control group. Results are as shown in Table 6.

TABLE 6

Prolongation Effect on Time of Gasping Movements Induced by Complete Ischemia in Mice (p.o.)

| Compound No. | Dose (mg/kg) | Average Persistent Time (second ± standard error) | Rate of Change |
|---|---|---|---|
| 1 | control | 19.0 ± 0.3 | 100.0 ± 1.6 |
|   | 0.3 | 20.2 ± 0.7 | 106.3 ± 3.7 |
|   | 1.0 | 20.8 ± 0.5 | 109.5 ± 2.6 |
|   | 3.0 | 22.8 ± 0.3 | 120.0 ± 1.6 |
| 4 | control | 19.0 ± 0.3 | 100.0 ± 1.6 |
|   | 0.3 | 21.2 ± 1.0 | 111.6 ± 5.3 |
|   | 1.0 | 22.4 ± 0.9 | 117.9 ± 4.7 |
|   | 3.0 | 22.8 ± 0.4 | 120.0 ± 2.1 |
| 19 | control | 19.6 ± 0.4 | 100.0 ± 2.0 |
|   | 0.1 | 21.5 ± 0.5 | 109.7 ± 2.6 |
|   | 0.3 | 22.2 ± 0.4 | 113.3 ± 2.0 |
|   | 1.0 | 23.0 ± 0.6 | 117.3 ± 3.1 |

(iii) Other Experimental Example (a) Compounds 1, 4 and 19 show life-prolongation effect when death is induced by hypobaric hypoxia under reduced pressure (160 mmHg in mice, by oral administration at the dose of 3.0, 1.0 and 0.3 mg/kg body weight, respectively.

(b) Compounds 1, 4 and 19 show life-prolongation effect when death is induced by intraperitoneal administration of potassium cyanide (12.5 mg/kg body weight) in mice, by oral administration at the dose of 1.0, 1.0 and 0.3 mg/kg body weight, respectively.

(c) Compounds 1, 4 and 19 show inhibitory effect on the decrease of creatine phosphate, adenosine triphosphate and glucose in brain of mice induced by hypoxia under a low oxygent content gasous mixture composed of 4% of oxygen and 96% of nitrogen, by oral administration at the dose of 3.0, 0.3 and 1.0 mg/kg body weight, respectively.

EXPERIMENTAL EXAMPLE 3

Persistence of Protective Effect on Brain Anoxia

Prolongation Effect on Time of Gasping Movements Induced by Complete Ischemia in Mice One group comprised five STD-ddY male mice weighing 20-24 g. A solution obtained by dissolving an amount of a compound (Compound No. 1,4) in 0.1 ml of ethanol and then diluting the solution with a 0.1M glycine-sodium hydroxide buffer solution (pH 10.0) was subcutaneously administered in a proportion of 0.1 ml per 10 g of the body weight of a mouse. A solution obtained by dissolving an amount of a compound (Compound No. 19) in distilled water was orally administered in the same proportion as above. After 0.25, 0.5, 1, 2, 4, 6 and 8 hours for Compound No. 1 and 4, respectively, and after 0.25, 0.5, 1, 2, 4 and 6 hours for Compound No. 19, from administration, the neck of the mouse was cut with scissors for decapitation and, the persistent time until gasping movements, which appeared at the separated head, disappeared was measured. For comparison, a 0.1M glycine-sodium hydroxide buffer solution containing the same concentration of ethanol as the test solution, or distilled water, was likewise administered to the control group. Results are as shown in Table 7.

TABLE 7

Prolongation Effect on Time of Gasping Movements Induced by Complete Ischemia in Mice

| Compound No. | Dose (mg/kg), route | Time after Administration(hrs) | Average Persistent Time (second ± standard error) |
|---|---|---|---|
| 1 | control |  | 19.8 ± 0.4 |
|   | 3.0 (s.c.) | 0.25 | 22.6 ± 2.1 |
|   |   | 0.5 | 25.2 ± 1.0 |
|   |   | 1.0 | 26.2 ± 1.5 |
|   |   | 2.0 | 27.2 ± 1.2 |
|   |   | 4.0 | 23.8 ± 1.4 |
|   |   | 6.0 | 20.8 ± 0.4 |
|   |   | 8.0 | 19.8 ± 0.7 |
| 4 | control |  | 18.8 ± 0.4 |
|   | 3.0 (s.c.) | 0.25 | 24.2 ± 0.7 |
|   |   | 0.5 | 24.4 ± 0.8 |
|   |   | 1.0 | 26.2 ± 1.4 |
|   |   | 2.0 | 27.6 ± 0.9 |
|   |   | 4.0 | 25.6 ± 1.2 |
|   |   | 6.0 | 22.6 ± 0.8 |
|   |   | 8.0 | 19.6 ± 0.4 |
| 19 | control |  | 18.4 ± 0.3 |
|   | 3.0 (p.o.) | 0.25 | 23.0 ± 1.5 |
|   |   | 0.5 | 26.0 ± 2.5 |
|   |   | 1.0 | 28.1 ± 1.7 |

TABLE 7-continued

Prolongation Effect on Time of Gasping Movements Induced by Complete Ischemia in Mice

| Compound No. | Dose (mg/kg), route | Time after Administration(hrs) | Average Persistent Time (second ± standard error) |
|---|---|---|---|
| | | 2.0 | 30.8 ± 2.8 |
| | | 4.0 | 23.0 ± 0.9 |
| | | 6.0 | 18.8 ± 0.7 |

PREPARATIVE EXAMPLE 1

50mg of 16,19-ethano-$\omega$-dihomo-6,9$\alpha$-nitrilo-PGI$_1$ methyl ester (Compound No. 1) was dissolved in 10 ml of ethanol. The solution was mixed with 18.5 g of mannitol. After passing the mixture through a 30 mesh sieve and drying at 30° C. for 90 minutes, the mixture was again passed through a 30 mesh sieve.

To the powder obtained 200 mg of Aerosil (microfine silica) was added and the mixture was filled into 100 No. 3 hard gelatin capsules to obtain gastric capsules containing 0.5 mg of 16,19-ethano-$\omega$-dihomo-6,9$\alpha$-nitrilo-PGI$_1$ methyl ester (Compound No. 1) per capsule.

PREPARATIVE EXAMPLE 2

0.5 mg of 16,19-ethano-$\omega$-dihomo-6,9$\alpha$-nitrilo-PGI$_1$ methyl ester (Compound No. 1) was dissolved in 5 ml of ethanol and the solution was sterilized by filtration through a bacteria-retaining filter. The solution was placed in 0.1 ml portions in 1 ml ampoules to obtain ampoules each containing 10 $\mu$g of 16,19-ethano-$\omega$-dihomo-6,9$\alpha$-nitrilo-PGI$_1$ methyl ester (Compound No. 1) the ampoules were then sealed. The content of each ampoule after dilution to an appropriate volume, e.g., by diluting with a tris-hydrochloric acid buffer solution (pH 8.6) to 1 ml, is suitable for use as an injectable solution.

PREPARATIVE EXAMPLE 3

To a solution of 50 mg of 16,19-ethano-$\omega$-dihomo-6,9$\alpha$-nitrilo-PGI$_1$ methyl ester (Compound No. 1) and 1.6 g of $\alpha$-cyclodextrin in 10 ml of distilled water, 10 mg of citric acid, 50 g of lactose and 800 ml of distilled water were added to obtain a solution and distilled water was added thereto to make the total volume 1 liter. Thereafter, sterile filtration was performed in a conventional manner and the solution was placed, in 1 ml portions, in ampoules. After freeze drying, the ampoules were sealed to obtain a freeze dried preparation suitable for use, after dissolution, as an injectable solution.

PREPARATIVE EXAMPLE 4

In a manner similar to that described in Preparative Examples 1, 2 and 3, gastric capsules, injectable solutions and freeze dried preparations were produced using Compound Nos. 2 to 6.

PREPARATIVE EXAMPLE 5

0.5 mg of 15-cyclohexyl-$\omega$-pentanor-PGI$_2$ methyl ester (Compound No. 7) was dissolved in 5 ml of ethanol and the solution was sterilized through a bacteria-retaining filter. The solution was placed in 0.1 ml portions in 1 ml ampoules to obtain ampoules each containing 10 $\mu$g of 15-cyclohexyl-$\omega$-pentanor-PGI$_2$ methyl ester (Compound No. 7). The ampoules were then sealed. The content of each ampoule, after dilution to an appropriate volume, e.g. by diluting with a trishydrochloric acid buffer solution (pH 8.6) to 1 ml, is suitable for use as an injectable solution.

PREPARATIVE EXAMPLE 6

To a solution of 50 mg of 15-cyclohexyl-$\omega$-pentanor-PGI$_2$ methyl ester (Compound No. 7) and 1.6 g of $\alpha$-cyclodextrin in 10 ml of a 1% (v/v) solution of triethylamine in water, 50 g of lactose and 800 ml of a 1% (v/v) solution of triethylamine in water were added to obtain a solution and a 1% (v/v) solution of triethylamine in water was added thereto to make the total volume 1 liter. Thereafter, sterile filtration was performed in a conventional manner and the solution was placed, in 1 ml portions, in ampoules. After freeze drying, the ampoules were sealed to obtain a freeze dried preparation suitable for use, after dissolution, as an injectable solution.

PREPARATIVE EXAMPLE 7

In a manner similar to that described in Preparative Examples 5 and 6, injectable solutions and freeze dried preparations were produced also using Comound Nos. 8 to 16.

PREPARATIVE EXAMPLE 8

50 mg of 17(S)-methyl-$\omega$-homo-trans-$\Delta^2$-PGE$_1$ (Compound No. 18) was dissolved in 10 ml of ethanol. The solution was mixed with 18.5 g of mannitol. After passing the mixture through a 30 mesh sieve and drying at 30° C. for 90 minutes, the mixture was again passed through a 30 mesh sieve.

To the powder obtained, 200 mg of Aerosil (microfine silica) was added and the mixture was filled into 100 No. 3 hard gelatin capsules to obtain gastric capsules containing 0.5 mg of 17(S)-methyl-$\omega$-homo-trans-$\Delta^2$-PGE$_1$ (Compound No. 18) per capsule.

PREPARATIVE EXAMPLE 9

0.5 mg of 17(S)-methyl-$\omega$-homo-trans-$\Delta^2$-PGE$_1$ (Compound No. 18) was dissolved in 5 ml of ethanol and the solution was sterilised by filtration through a bacteria retaining filter. The solution was placed in 0.1 ml portions in 1 ml ampoules to obtain ampoules each containing 10 $\mu$g of 17(S)-methyl-$\omega$-homo-trans$\Delta^2$-PGE$_1$ (Compound No. 18). The ampoules were then sealed. The content of each ampoule, after dilution to an appropriate volume, e.g., by diluting with a tris-hydrochloric acid buffer solution (pH 8.6) to 1 ml, is suitable for use as an injectable solution.

PREPARATIVE EXAMPLE 10

To a solution of 50 mg of 17(S)-methyl-$\omega$-homo-trans-$\Delta^2$-PGE$_1$ (Compound No. 18) and 1.6 g of $\alpha$-cyclodextrin in 10 ml of distilled water, 10 mg of citric acid, 50 g of lactose and 800 ml of distilled water were added to obtain a solution and distilled water was added thereto to make the total volume 1 liter. Thereafter, sterile filtration was performed in a conventional manner and the solution was placed, in 1 ml portions, in ampoules. After freeze drying, the ampoules were sealed to obtain a freeze dried preparation suitable for use, after dissolution, as an injectable solution.

PREPARATIVE EXAMPLE 11

In a manner similar to that described in Preparative Examples 8, 9 and 10, gastric capsules, injectable solutions and freeze dried preparations were produced using Compound Nos. 17 and 19 to 27.

It is to be understood that the expression 'brain cells' as used in this specification and the accompanying claims includes brain nerve cells and other brain cells.

We claim:

1. A method for the prevention or treatment of anoxia of brain cells in a mammalian host which comprises administering to a host subject to, or suffering from said anoxia, an effective amount of a prostaglandin derivative selected from a $PGI_1$ derivative of the formula:

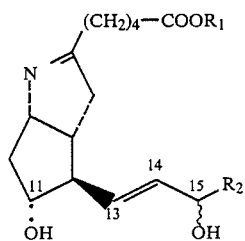

wherein $R_1$ represents a hydrogen atom or a lower alkyl group and $R_2$ represents a 2-methylhexyl group, a 3-propylcyclopentyl group, a 3-butylcyclopentyl group or a 4-propylcyclohexyl group, a $PGI_2$ derivative of the formula:

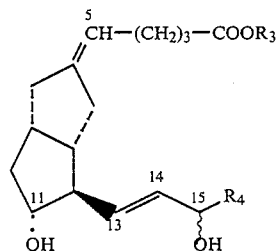

wherein $R_3$ represents a hydrogen atom or a lower alkyl group and $R_4$ represents a 2-methylhexyl group, a cyclopentyl group, a 3-propylcyclopentyl group or a cyclohexyl group, a $PGI_2$ derivative of the formula:

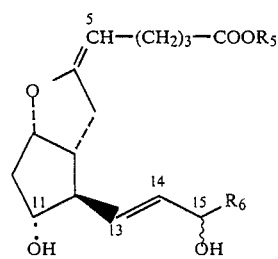

wherein $R_5$ represents a lower alkyl group and $R_6$ represents a pentyl group, a 1-methylpentyl group, a 1-methyl-5-chloropentyl group, a 2-methyl-5-chloropentyl group, a 3-ethylcyclopentyl group, a 3-propylcyclopentyl group, a 3-butylcyclopentyl group, a 3-(2-chloroethyl)cyclopentyl group, a cyclohexyl group, a 4-ethylcyclohexyl group or a cyclohexylmethyl group, or a $PGE_1$ derivative of the formula:

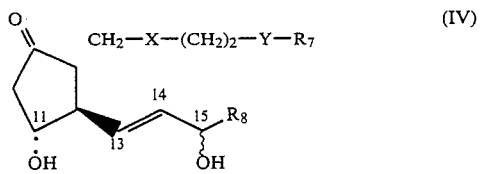

wherein

X represents a methylene group or a carbonyl group, and (i) when X represents a methylene group, Y represents an ethylene group or a trans-vinylene group, $R_7$ represents a carboxyl group or a lower alkoxycarbonyl group and $R_8$ represents a 2-methylhexyl group or a 1-cyclohexylethyl group, and (ii) when X represents a carbonyl group, Y represents an ethylene group, $R_7$ represents a carboxyl group, a lower alkoxycarbonyl group, a glycoloyl group or a hydroxymethyl group and $R_8$ represents a 2-methylhexyl group, a cyclopentyl group, a 3-propylcyclopentyl group or a 3-butylcyclopentyl group, the double bonds between $C_{13}$–$C_{14}$ in formulae (I), (II), (III) and (IV) being trans, the configuration at $C_5$ in formulae II and III being E or Z or a mixture thereof, the hydroxy groups attached to the $C_{11}$ position in formulae (I), (II), (III) and (IV) being in α-configuration and the hydroxy groups attached to the $C_{15}$ position in formulae (I), (II), (III) and (IV) being in α- or β-configuration, or a mixture thereof, or a cyclodextrin clathrate of a derivative of formula (I), (II), (III) or (IV) or, when $R_1$ in formula (I) or $R_3$ in formula (II) represents a hydrogen atom, or when $R_7$ in formula (IV) represents a carboxy group, a non-toxic salt thereof.

2. A method according to claim 1 in which the prostaglandin derivative or cyclodextrin clathrate thereof or non-toxic salt thereof is administered orally or parenterally.

3. A method according to claim 1 in which the amount of prostaglandin derivative administered daily is from 0.0003 to 100 mg/kg body weight.

4. A method according to claim 3 in which the prostaglandin derivative is administered intravenously, intramuscularly or subcutaneously at a daily dose from 0.0003 to 10 mg/kg body weight.

5. A method according to claim 3 in which the prostaglandin derivative is administered orally at a daily dose from 0.0003 to 30 mg/kg body weight.

6. A method according to claim 1 in which the hydroxy groups attached to the $C_{15}$ position in the prostaglandin derivative of formulae (I), (II), (III) and (IV) is in α-configuration.

7. A method according to claim 1 in which, in formula (I), $R_1$ represents a hydrogen atom or a methyl group, in formula (II) $R_3$ represents a hydrogen atom or a methyl group, in formula (III) $R_5$ represents a methyl group, and in formula (IV) $R_7$ represents a carboxy or methoxycarbonyl group, 8. A method according to claim 1 in which the prostaglandin derivative is a $PGI_1$ derivative of formula (I) depicted in claim 1 or a $PGI_2$ derivative of formula (II) depicted in claim 1, or a cyclodextrin clathrate thereof, or when $R_1$ in formula (I) or $R_3$ in formula (II) represents a hydrogen atom, a non-toxic salt thereof.

9. A method according to claim 8 in which the prostaglandin derivative or cyclodextrin clathrate thereof, or non-toxic salt thereof, is administered orally.

10. A method according to claim 8 in which the prostaglandin derivative is 16,19-ethano-ω-dihomo-6,9α-nitrilo-PGI$_1$ methyl ester or 17(S)-methyl-ω-homo-6,9α-nitrilo-PGI$_1$, or a cyclodextrin clathrate thereof.

11. A method according to claim 1 in which the prostaglandin derivative is a PGI$_2$ derivative of formula (III) depicted in claim 1, or a cyclodextrin clathrate thereof.

12. A method according to claim 11 in which the prostaglandin derivative is administered parenterally.

13. A method according to claim 11 in which the prostaglandin derivative is 15-cyclohexyl-ω-pentanor-PGI$_2$ methyl ester or 16,19-ethano-ω-homo-PGI$_2$ methyl ester, or a cyclodextrin clathrate thereof.

14. A method according to claim 1 in which the prostaglandin derivative is a PGE$_1$ of general formula (IV) depicted in claim 1, or a cyclodextrin clathrate thereof, or when R$_7$ in formula (IV) represents a carboxyl group, a non-toxic salt thereof.

15. A method according to claim 14 in which the prostaglandin derivative is administered orally or parenterally.

16. A method according to claim 14 in which the prostaglandin derivative is 17(S)-methyl-ω-homo-trans-Δ$^2$-PGE$_1$, or a cyclodextrin clathrate thereof.

17. A method according to claim 1 in which the prostaglandin derivative is 16,19-ethano-ω-dihomo-6,9α-nitrilo-PGI$_1$ methyl ester, 17(S)-methyl-ω-homo-6,9α-nitrilo-PGI$_1$, 15-cyclopentyl-ω-pentanor-5E-6,9α-methano-PGI$_2$, 15-cyclohexyl-ω-pentanor-PGI$_2$ methyl ester, 16,19-ethano-ω-homo-PGI$_2$ methyl ester, 17(S)-methyl-ω-homo-trans-Δ$^2$-PGE$_1$, 15-cyclopentyl-ω-pentanor-6-keto-PGE$_1$ methyl ester, 2-decarboxy-2-glycoloyl-15-cyclopentyl-ω-pentanor-6-keto-PGE$_1$, 17(S)-methyl-ω-homo-6-keto-PGE$_1$ alcohol, or 16,18-ethano-ω-dihomo-6-keto-PGE$_1$ alcohol, or a cyclodextrin clathrate thereof.

18. A method according to claim 1 in which the prostaglandin derivative is 16,18-ethano-ω-homo-6,9α-nitrilo-PGI$_1$, 17(S)-methyl-ω-homo-6,9α-nitrilo PGI$_1$ methyl ester, 17-(S)-methyl-ω-homo-6,9α-methano-5EZ-PGI$_2$ methyl ester, PGI$_2$ methyl ester, 16,18-ethano-ω-homo-PGI$_2$ methyl ester, 17(R)-methyl-20-chloro-PGI$_2$ methyl ester, 16,18-ethano-ω-dihomo-PGI$_2$ methyl ester, 16,18-ethano-20-chloro-PGI$_2$ methyl ester, 16-cyclohexyl-ω-tetranor-PGI$_2$ methyl ester, 16(ξ)-methyl-20-chloro-PGI$_2$ methyl ester, 16,18-ethano-PGI$_2$ methyl ester, 16-cyclohexyl-ω-trinor-PGE$_1$ methyl ester, 16,18-ethano-ω-dihomo-6-keto-PGE$_1$ methyl ester, 2-decarboxy-2-glycoloyl-17(S)-methyl-ω-homo-6-keto-PGE$_1$, 2-decarboxy-2-glycoloyl-16,18-ethano-ω-homo-6-keto-PGE$_1$, 16,18-ethano-ω-homo-6-keto-PGE$_1$ alcohol, or a cyclodextrin clathrate thereof or, when such a salt exists, a non-toxic salt thereof.

* * * * *